United States Patent [19]

Prodi

[11] Patent Number: 4,704,527

[45] Date of Patent: * Nov. 3, 1987

[54] DEVICE FOR THE SEPARATION OF AIRBORNE PARTICLES INTO GRAIN SIZE CLASSES

[76] Inventor: Vittorio Prodi, Via Martinelli, 7, 40137 Bologna, Italy

[*] Notice: The portion of the term of this patent subsequent to Aug. 19, 2003 has been disclaimed.

[21] Appl. No.: 723,745

[22] Filed: Apr. 16, 1985

[30] Foreign Application Priority Data

Apr. 19, 1984 [IT] Italy ................................. 3431 A/84

[51] Int. Cl.[4] ........................................... G01N 23/08
[52] U.S. Cl. ................................... 250/308; 250/304; 250/435
[58] Field of Search ...................... 250/308, 304, 435; 73/432 PS, 863.23

[56] References Cited

U.S. PATENT DOCUMENTS

| | | | |
|---|---|---|---|
| 3,854,321 | 12/1974 | Dahneke | 73/432 PS |
| 3,952,207 | 4/1976 | Leschonski et al. | 73/432 PS |
| 4,213,852 | 7/1980 | Etkin | 73/432 PS |
| 4,298,836 | 11/1981 | Groves et al. | 73/432 PS |
| 4,606,232 | 8/1986 | Prodi | 73/863.23 |

Primary Examiner—Carolyn E. Fields
Assistant Examiner—Richard Hanig
Attorney, Agent, or Firm—Omri M. Behr

[57] ABSTRACT

A device is described for the separation of airborne particles, such as particles of an aerosol, into grain size classes.

The main characteristic of the present invention lies in the fact that it comprises:

a first body in which there is formed an L-shape channel defined by a first cavity from which, in use, filtered air is ejected into a second cavity thereof formed on the lower surface of the said first body;

a second body having an upper surface in contact with the lower surface of the said first body;

a third cavity formed in the said second body in correspondence with the said second cavity and in which there is created a depression;

a rectangular plate the upper surface of which is flat and the edge of which is fixed by adhesive to the edge of the said third cavity for delimiting the said second cavity from below, there being formed a plurality of through slits in the said plate; and a nozzle operable to inject a quantity of aerosol into the said first cavity in proximity with the connection of this with the said second cavity.

16 Claims, 6 Drawing Figures

DEVICE FOR THE SEPARATION OF AIRBORNE PARTICLES INTO GRAIN SIZE CLASSES

BACKGROUND OF THE INVENTION

The present invention relates to a device for the separation of airborne particles, such as those in an aerosol, into grain size classes.

Devices of the above indicated type are instruments which separate the particles still in suspension into grain size classes and collect them, whilst maintaining the separation, on a filter. It is then possible to perform a series of chemical and physico-chemical analyses on the deposited particles in dependence on the dimensions of these for the purpose of determining the risk resulting from inhalation of dust in the environment in which they are present. The said devices are therefore utilized in the testing of environmental and industrial health, in medical physics and in powder technology generally.

The devices currently in the market in the United States for commercial usage, consist, schematically, of a rectangular channel having a substantially L-shape configuration, traversed by filtered air. This channel then has two parts the first of which is defined by a first nozzle which ejects filtered air into the second part which is delimited above by a body and below by a support plate on which a filter is positioned. Within the first nozzle there is positioned a second nozzle which ejects the particle-bearing air such as an aerosol. The introduction of the aerosol takes place therefore upstream of the curvature of the said channel. This means that as the particles travel past the curved part of the channel they are separated in dependence on their aerodynamic dimensions into various streams. Each stream is composed of particles of the same aerodynamic diameter. Such streams are subsequently deposited on filters starting from the stream with the particles of greater diameter. The support plate is rectangular and is made in stainless steel. This plate is supported by a pipe union, and, more precisely, rests on a flange extending from the said pipe union.

The devices described above have various serious disadvantages.

In particular, since the plate rests freely on the flange of the pipe union, and since this, being of reduced dimensions, is difficult to work and therefore has certain tolerances, there is obtained an air space between the plate and the body of different thickness which prejudices the correct operation of the device, and it can happen that an irregular deposition of the particles of the aerosol takes place. In fact, for a correct operation of the device, it is necessary that the channel delimited by the plate and by the said body should have a constant height. The plate must therefore be edgewise with the edge of the flange and must be flat. But, since the sintered plate is made of stainless steel, grinding to make it coplanar is difficul to do in that the material of which it is made has a certain degree of elasticity. This involves the possibility of differentiated deposits of particles on the filter. It is also necessary to note that setting up of the plate onto the flange is manual and this can involve difficulty and positioning errors of this plate. Finally, the fact that the material of which the plate is made has characteristics of elasticity can involve buckling of this towards the interior of the pipe union because of the pressure difference existing between the interior of the channel and the interior of the pipe union.

SUMMARY OF THE INVENTION

The object of the present invention is to provide a device for the separation of airborne particles into grain size classes which will be free from the above mentioned disadvantages and which will comprise a support plate the upper surface of which, delimiting the channel, will be perfectly flat and for which there will be no setting up operations necessary.

Other objects and advantages of the present invention will become apparent from the following description.

According to the present invention there is provided a device for the separation of airborne particles into grain size classes, characterised by the fact that it comprises:

a first body in which there is formed a substantially L-shape channel, having a first part defined by a first cavity from which, in use, a quantity of filtered air is ejected into a second cavity formed on the lower surface of the said first body;

a second body having an upper surface in contact with and facing the lower surface of the said first body;

a third cavity formed in the said second body in correspondence with the said second cavity and in which there is caused a pressure lower than that existing in the said channel;

a rectangular plate fixed, preferably by means of an adhesive, onto the edge of the said third cavity and serving to delimit the said second cavity from below, on the said plate there being formed a plurality of through slots and its upper surface being flat; and a nozzle connected to a source of particle-bearing air and operable to inject into the said first cavity, close to the connection of this with the said second cavity, a quantity of particle-bearing air in such a way that the particles present in suspension in the air are drawn by the filtered air towards the said second cavity and these, on passing the same direction, are separated along the fluid streams according to their aerodynamic diameter.

BRIEF DESCRIPTION OF THE DRAWINGS

For a better understanding of the present invention a preferred embodiment will now be described, purely by way of non limitative example, with reference to the attached drawings, in which:

FIG. 7 is a detail which is an alternate to that of FIG. 6.

DETAILED DESCRIPTION OF THE INVENTION

Figures 1, 6:
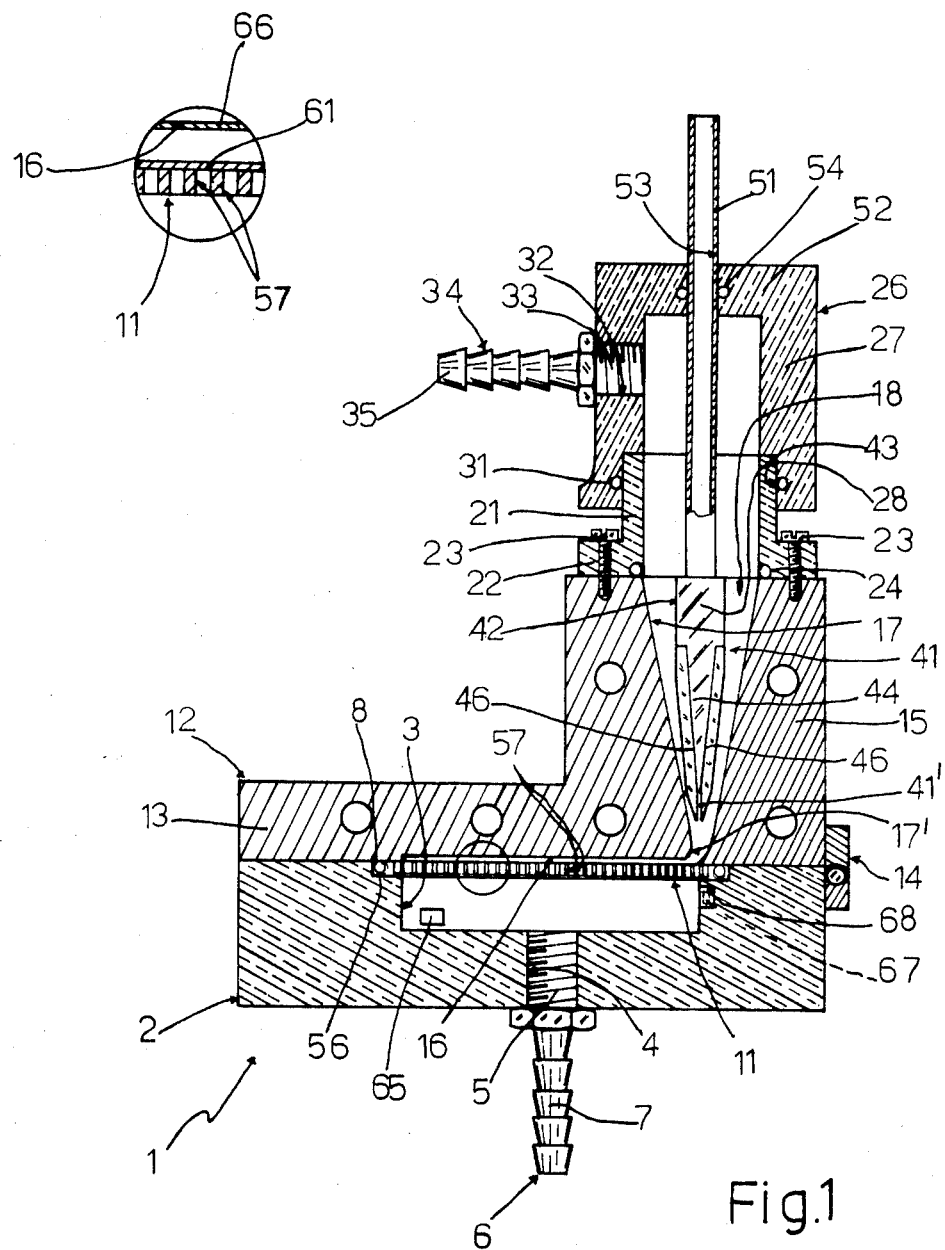
FIG. 1 is a section of a device for the separation of airborne particles into grain size classes.
FIG. 6 is a view on an enlarged scale of a third detail of the device of FIG. 1.
Figure 3:
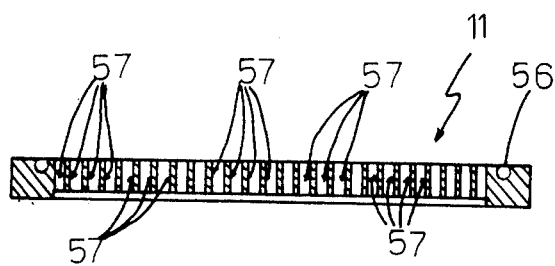
FIGS. 2 and 3 are, respectively, a plan view and a section of a detail of the device of FIG. 1.
Figure 2:
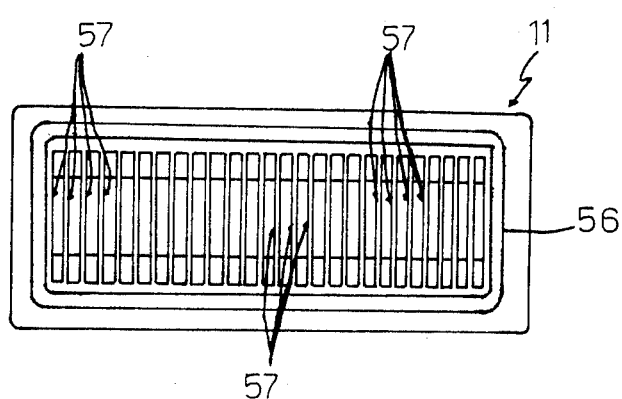

As illustrated in FIG. 1, the reference numeral 1 indicates as a whole a device for the separation of airborne particles such as particles of an aerosol into grain size classes. The device 1 comprises a base body 2 of substantially prismatic form and in which, in correspondence with its upper face, there is formed a cavity 3 also of prismatic form. In the central part of the base surface of the cavity 3 there is formed a threaded through hole 4 into which is screwed the upper part 5 of a pipe union 6 having a lower part 7 projecting from the hole 4 at the lower face of the body 2. In the upper edge of the cavity 3 there is formed a recess 6 on the lower surface of which there is fixed a plate 11 which will be described hereinbelow with reference to FIGS. 2 and 3. On the base body 2 rests an upper body 12 which in section has a substantially L-shape configuration having a substantially prismatic lower portion 13 the lower face of which faces the upper face of the body 2. The body 12 is pivoted, by means of a pivot 14, at a lateral face of the portion 13 to a lateral face of the body 2. The body 12 further includes a prismatic portion 15 which extends upwardly from a lateral zone of the upper face of the portion 13. On the lower face of this latter there is formed a shallow prismatic cavity 16 facing the cavity 3 of the body 2. Along the longitudinal axis of the portion 15 there is formed a through cavity 17. This latter has a section with rectangular outline but with two opposite sides the length of which decreases gradually in progressing from the top towards the bottom. The cavity 17 communicates with the cavity 16 close to the lower face of the portion 13. The cavities 16 and 17 thus define a channel 18 having an L-shape configuration and the inner surfaces of which relating to the passage between them are rounded in such a way as to join the mouth of the cavity 17 into the cavity 16.

As will be seen better below the cavity 17 constitutes a nozzle through which a quantity of filtered air coming from an external source is ejected into the cavity 16. For a better understanding the part of the channel 18 relating to the passage of the filtered air between the cavities 17 and 16 will be called the "mouth" hereinbelow and indicated with the reference numeral 17'. At the upper end of the portion 15 there is fixed, coaxially thereto, a sleeve 21 communicating internally with the channel 18. In detail, the sleeve 21 has a flange 22 at its lower end fixed by means of screws 23 to the upper end of the portion 15. Between this and the flange 22 there is formed a seat for housing a sealing ring 24. On the sleeve 21 there is fixed a plug 26 of substantially cup-shape configuration with the internal cavity facing downwardly. The plug 26 has a recess 28 along the inner surface of its lateral part 27, which can be engaged by the upper end of the sleeve 21. Within the interior of the recess 28 there is formed a seat for a sealing ring 31. On the lateral part 27 of the plug 26 there is formed a threaded hole 32 into which is screwed a threaded portion 33 of a pipe union 34 a second portion 35 of which is external to the plug 26 and is connectible by means of a duct (not illustrated) with the said source of filtered air.

Figure 5:
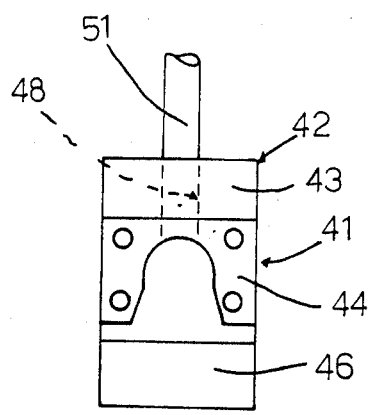
FIG. 5 is a front view of the detail of FIG. 4 from which one component has been removed.
Figure 4:
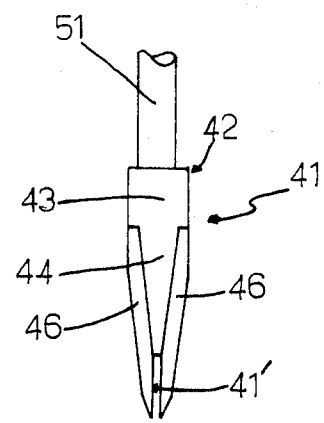
FIG. 4 is a side view of a second detail of the device of FIG. 1.

As illustrated in FIGS. 1, 4 and 5, the device 1 includes a second nozzle 41 positioned in correspondence with the cavity 17. In use, by means of the nozzle 41, a quantity of aerosol is ejected into the channel 18 and, more precisely, into the cavity 17 close to the mouth 17'. The nozzle 41 comprises a central portion 42 having an upper part 43 constituted by a small prismatic plate and a lower part 44 constituted by a plate of thickness decreasing from the top towards the bottom and of substantially U-shape configuration with the concavity facing downwardly (FIG. 5). On the central portion 42 and more precisely on the lower part 44 there are fixed, for example by means of screws, a respective blade 46 on each of its faces of greater extent. The blades 46 extend beyond the lower end of the part 44 and delamit laterally the inner recess of the part 44. The lower ends of the blades 46 are substantially parallel to one another and define an outlet 41' of the nozzle 41. It is to be noted that the longitudinal axis of the nozzle 41 is parallel to that of the cavity 17 and moreover is displaced towards the zone of the portion 13 in which the cavity 16 is formed in such a way that the outlet 41' of the nozzle 41 is closer to one inner wall of the cavity 17 rather than in an intermediate position. On the upper part 43 of the portion 42 there is formed a through hole 48 illustrated in broken outline in FIG. 5 and coaxial with the longitudinal axis of the nozzle 41. The hole 48 in particular communicates with the recess defined by the U-shape conformation of the lower part 44. From the upper part 43 in correspondence with the hole 48 and therefore communicating internally therewith there extends upwardly a duct 51 which internally traverses the sleeve 21 and the plant 26 and which extends beyond the upper part 52 of the plant 26 through a through hole 53 formed therein. In the hole 53 there is formed a seat for housing a sealing ring 54. The duct 51 is connected to a source of aerosol which in use could be the environment itself.

As illustrated in FIGS. 1, 2 and 3 the plate 11 is of rectangular outline and has around its edge a seating for a sealing ring 56. This later cooperates with the lower face of the portion 13 and, more precisely, with the zone of this face which delimits the cavity 16, in such a way as to avoid unwanted escape of filtered or and aerosol. In the plate 11 there are a plurality of through slots 57 aligned with one another in such a way as to have their longitudinal axes parallel to one another and parallel to the smaller side of the geometric figure representing the plate 11 itself. The mouth 17' of the cavity 17 is disposed in correspondence with this smaller side in such a way that the fluid composed of filtered air and aerosol which is ejected into the cavity 16, delimited below by the plate 11, encounters one slit 57 at a time. The slits 57 are obtained by means of milling operations which allows bodies such as the plate 11 even of very small thickness to be worked. It is, moreover, to be noted that with such working it is possible to arrange that the solid part of the plate 11 between two adjacent slots 57 is of very small thickness. Naturally, for this type of work, the openings of the slots 57 have a section which is decreasing from the top downwardly. In use, after the milling operations, the plate 11, or rather its edge, is secured by adhesive to the surfaces which define the recess 8. Subsequently the plate 11 is ground, that is to say the upper surface of the plate 11 is made flat and coplaner with the upper surface of the body 2 which is also ground either previously or during the grinding operations on the plate 11.

As illustrated in FIGS. 1 and 6, on the upper surface of the plate 11 there is arranged a filter 61 on the upper surface of which, in use, the particles present in the aerosol become deposited. The filter 61 is rectangular and covers the whole of the part of the plate 11 in which the slots 57 are formed. The filter 61 is preferably of the membrane type utilising a porous material such as cellulose or teflon.

The assembly and setting up of the device 1 as already partly described are easy to perform.

In particular, after the milling operations for the formation of the slots 57, the plate 11 is secured by adhesive onto the body 2. Subsequently, the upper surface of the plate 11 is ground and the filter 61 is positioned on it. Once the operation of the device 1 has been completed it is possible to extract the filter 61 which occupies a portion of the cavity 16, simply by making the body 12 turn in a clockwise sense about the edge of the body 2 where the hinge 14 is fitted.

The operation of the device 1 takes place in the following way.

In detail, a constant quantity of filtered air is chanelled into the cavity 17 from a suitable source, and from a second source, which could be the environment itself, a constant quantity of aerosol is injected, via the nozzle 41, into the cavity 17 in correspondence with the mouth 17'. This is possible, for example, by connecting the pipe union 6 and therefore the interior of the cavity 3 to a pump able to create a depression in the cavity 3 which draws in the filtered air and the aerosol. As is known, an aerosol is, for example, air in which there are present particles in suspension. The fluid constituted by the filtered air and the aerosol subsequently enters the cavity 16. Since this fluid, in order to arrive at the cavity 16, must tranverse a tight curvature (the mouth 17') it happens that the particles of dust present in the aerosol are separated in this according to the aerodynamic diameter into various bands of fluid, that is to say, all the particles of the same grain size class will be present along a fluid band. At the output of the mouth 17' the particles begin to be deposited on the filter 61 starting from the particles of greater diameter. The fluid, cleaned of particles, will first enter into the cavity 3 and subsequently will flow out of the device 1 through the pipe union 6 towards the said pump. On the filter 61 there is therefore obtained a deposit which is differentiated in dependence on the grain size class to which the particles belong. In particular, the particles of greater diameter will be deposited on the portion of the filter 61 closer to the mouth 17'. It is to be noted that the dust particles will deposit only in those portions of the filter 61 positioned in correspondence with the slits 57 and not over the whole of the filter 61, that is to say, the portions of the filter 61 positioned in correspondence with the solid parts of the plate 11 between two adjacent slots 57 will be excluded from deposits. It is therefore possible to sub-divide the filter 61, after removal, into various parts corresponding to the slits 57, and to make this sub-division it is only necessary simply to cut the filter 61 in correspondence with those parts thereof positioned in correspondence with the solid parts of the plate 11 and subsequently to cut the side parts of the filter 61 which are not usable due to the perturbing effect of the lateral walls of the cavity 16. The technique for the separation of the dust particles into grain size classes is known and described in various scientific publications some of which have been written by the inventor of the device 1. It lies in the fact that the particles traversing the curved part (the mouth 17') of the channel 18, tend by inertia to maintain their velocity in direction and sense but are drawn by the flow of fluid. The particles therefore separate into initial fluid bands upon leaving the nozzle 41, the separation of which is a function only of the aerodynamic diameter. The separation between particles of different diameters is, however, small at the output of the curved part (the mouth 17') of the channel 18. This does not allow a sufficient exploitation of this separation to enable even a minimum of information to be obtained. With the device 1, the separation between the particles of different diameter is, on the other hand, amplified since it makes use of a projection onto a wall (filter 61) downstream of the curvature of the channel 18, through which the fluid is drawn and filtered. The filter 61 therefore collects all the particles in different positions according to their aerodynamic diameters. The particles of smaller diameter are collected in those parts of the filter 61 furthest from the mouth 17' and the information pertinent to them does not become lost as happened in similar devices to that of the subject of the present invention. It is to be noted, finally, that for a correct operation of the device 1, that is to say to obtain a greater separation of the particles into the various grain size classes, the longitudinal axis of the nozzle 41 is displaced towards the wall of the cavity 17 closest to the part of the portion 13 in which the cavity 16 is formed. This characteristic is determined experimentally and is described in the said publications. Subsequently to the deposition of the particles the filter 61 is extracted from the device 1 and all the chemical and/or physico-chemical analyses necessary for industrial and environmental health, medical physics and dust technology generally are done. The aerodynamic separation of the particles can be used to study the mass and activity of these particles or else by means of observations through optical or electronic microscopes it is possible to determine the form, density and other characteristics of the particles themselves.

With reference to FIG. 1, by utilising the device 1 it is possible to apply the $\beta$ absorption technique for the determination in real time of the mass of particles deposited on the filter 61. To apply this technique it is sufficient to dispose in the cavity 3 a source 65 of $\beta$ radiation and in the cavity 16 a detector 66 (FIG. 6), for example of the surface barrier diode type. The solid parts of the plate 11 in this case serve as collimators for the radiation emitted from the source 65. This latter could be of dimensions such as to occupy the whole of the length of the cavity 3 or else may be of small dimensions as illustrated in FIG. 1 but slidable along the cavity 3.

By utilising the device 1 it is possible to obtain an optical reading for the determination in real time of the quantity of particles in each grain size class. To obtain the optical reading it is necessary to remove the filter 61 and to employ a photometer 67 illustrated in broken outline in FIG. 1. The photometer 67 which can be of the laser beam type is lodged in a reces 68 formed in one side face of the cavity 3. Although the filter is not there the plate 11 permits the particles to be separated into grain size classes by maintaining them in suspension. At the outlet of the slots 57 with the photometer 67 it is possible to determine the number of particles for each grain size class. If a second plate 11' is fixed in the cavity 3 in a lower position than that of the plate 11 and the space concerned with the photometer 67, on which is positioned a filter 61' similar to the filter 61, it is then possible to analyse the deposit of particles on such filter thus obtaining the maximum information both in real time on the quantity and in a subsequent time on the composition and activity. It is also possible to utilise in this case a filter which is not of the membrane type, but one formed with a material which can support high temperatures such as, for example, glass fibre. With such a filter the use of the device 1 can be extended even into places or environments at high temperatures such as, for example, chimneys.

From what has been explained above, the numerous advantages consequent on the arrangement of the present invention will become apparent.

In particular, the plate 11 is secured by adhesive to the body 2 and therefore there are no setting up operations required. As well as the fact that it is fixed, the plate 11 can be ground in such a way as to make its upper surface flat and coplanar with the upper surface of the body 2. This permits the plate 11 to be worked with the mechanical precision required and therefore allows a greater control of it in the constructional phase to be obtained. Moreover, the filter 61 is occluded along the solid parts of the plate 11. This constitutes a reference in cutting the filter 61 for the analyses which are subsequently performed on the deposit. With the device 1 it is possible to use the β absorption technique for the determination in real time of the number of particles deposited. It is further possible, by means of the photometer 67, to obtain an optical reading. Finally, as already described, the device 1 can be utilised even in environments having very high temperatures, with the use of a filter of suitable material.

Finally, it is clear that the device 1 described and illustrated here can be modified and varied without by this departing from the protective scope of the present invention.

I claim:

1. A device employing a source of filtered air, a source of negative pressure and a source of particle-bearing air for the separation of airborne particles into grain size classes, characterized by the fact that it comprises a first body having an upper and lower surface and in which is formed a substantially L-shape channel, said channel having a first part defining a first cavity from which, in use, is ejected a quantity of filtered air, said channel having a second part positioned downstream of said first cavity to receive filtered air ejected therefrom, said second part of the channel defining a second cavity formed on the lower surface of said first body;

a second body having an upper surface facing and in contact with the lower surface of said first body, said second body having formed in it a third cavity in correspondence with said second cavity, said third cavity having a port adapted to connect to said source of negative pressure, said first and second cavity being joined at a cavity connection;

a rectangular plate secured onto the edge of and placed into said third cavity and operable to delimit the lower part of said second cavity, there being formed on said plate a plurality of through slots having á flat upper surface; and a nozzle having an inlet adapted to be connected to said source of particle-bearing air and operable to inject a quantity of such particle-bearing air into said first cavity close to the second cavity to allow the particles present in suspension in the air near said cavity connection to be drawn by the filtered air towards said second cavity, said first and second cavity being placed at an angle requiring the particles to turn, the sharper the turn made by the particles the deeper into said second cavity and the further away from said cavity connection they travel, so that after having passed said cavity connection the particles are separated into fluid bands according to their aerodynamic diameter.

2. A device according to claim 1, characterized by the fact that the said slots have their longitudinal axes parallel to one another and orthogonal to the longitudinal axis of the first cavity in such a way that any fluid at the output of the said connection meets a whole slot at a time.

3. A device according to claim 2, characterized by the fact that the upper surface of the said plate is coplanar with the upper surface of the said second body.

4. A device according to claim 2, characterized by the fact that the lognitudinal axis of said nozzle is parallel to that of said first cavity and is close to its lateral wall nearest to said second cavity.

5. A device according to claim 4, characterized by the fact that the said first cavity has a substantially rectangular section, two opposite sides of which are of decreasing length from the top downwardly.

6. A device according to claim 1, characterized by the fact that the said second cavity is prismatic.

7. A device according to claim 1, characterized, by the fact that said third cavity is prismatic; the interior of said third cavity being adapted to be connected to said source of negative pressure.

8. A device according to claim 1, characterized by:

a duct, said nozzle including a central portion having an upper part in which is formed a first through-hole the interior of which is in communication via said duct with said source of particle-bearng air, said central portion of said nozzle having a lower part which is in a substantially U-shape configuration in such a way that said first through-hole opens into the concavity defined by the U-shape form thereof; and a pair of blades affixed on respective opposite faces of said lower part in a position to delimit laterally the flow path for the particle bearing air.

9. A device according to claim 8, characterized by:

a sealing plug affixed on the first body in correspondence with the upper end of said first cavity, said sealing plug having a second hole through which said duct projects to connect with the source of particle-bearing air, and a third hole forming a seating; and a pipe union seated in said third hole and operable to put the interior of said plug and therefore said first cavity into communication with the source of filtered air.

10. A device according to claim 1, characterized by the fact that the upper surface of the said plate supports a filter on which, in use, the particles are deposited according to their various grain size classes.

11. A device according to claim 10, characterized by the fact that said filter is of the membrane type, formed with a porous material.

12. A device according to claim 10, characterized by:

a source of radiation housed within the interior of said third cavity; and a detector means being located on the upper part of said second cavity to obtain, in use, a determination in real time of the number of particles which are deposited on said filter.

13. A device according to claim 12, characterized by the fact that the said source of $\beta$ radiation is slidable along the longitudinal axis of the said third cavity for the determination of the number of particles deposited on the portion of the said filter associated with a predetermined slot of the said plate.

14. A device according to claim 1, characterized by:

a photometer means fixed on one lateral wall of said third cavity for illuminating the particles leaving said second cavity and to optically sense the particle density at said slot of the said plate.

15. A device according to claim 14, characterized by:

a grate shaped similar to said plate positioned in said third cavity parallel to and downstream from said plate, said grate being positioned downstream from the region of said third cavity over which said photometer performs its detection; and a second filter deposited on said grate and on which, in use, the particles are deposited.

16. A device according to claim 15, characterized by the fact that said second filter comprises a material resistant to high temperatures.

* * * * *